US011197965B2

(12) United States Patent
Dellaca et al.

(10) Patent No.: US 11,197,965 B2
(45) Date of Patent: Dec. 14, 2021

(54) METHOD AND SYSTEM FOR THE ADMINISTRATION OF A PULMONARY SURFACTANT BY ATOMIZATION

(71) Applicant: CHIESI FARMACEUTICI S.p.A., Parma (IT)

(72) Inventors: Raffaele Dellaca, Parma (IT); Ilaria Milesi, Parma (IT); Mario Di Cecio, Parma (IT); Roger Fane Sewell, Parma (IT); Donal Joseph Taylor, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 892 days.

(21) Appl. No.: 15/028,670

(22) PCT Filed: Oct. 16, 2014

(86) PCT No.: PCT/EP2014/072278
§ 371 (c)(1),
(2) Date: Apr. 11, 2016

(87) PCT Pub. No.: WO2015/059037
PCT Pub. Date: Apr. 30, 2015

(65) Prior Publication Data
US 2016/0263333 A1  Sep. 15, 2016

(30) Foreign Application Priority Data
Oct. 22, 2013 (EP) .................................. 13189768

(51) Int. Cl.
*A61M 11/00* (2006.01)
*A61M 16/04* (2006.01)
(Continued)

(52) U.S. Cl.
CPC ...... *A61M 11/007* (2014.02); *A61M 16/0486* (2014.02); *A61M 16/06* (2013.01);
(Continued)

(58) Field of Classification Search
CPC .. A61M 11/00; A61M 11/001; A61M 11/007; A61M 11/006; A61M 11/02;
(Continued)

(56) References Cited

U.S. PATENT DOCUMENTS 3,794,026 A * 2/1974 Jacobs .............. A61M 16/0465
128/200.13
4,567,882 A * 2/1986 Heller ................... A61M 25/01
128/200.26
(Continued)

FOREIGN PATENT DOCUMENTS

EP 0 692 273 A1 1/1996
EP 0692273 A1 * 1/1996 ........ A61M 16/0463
(Continued)

OTHER PUBLICATIONS

International Search Report and Written Opinion of the International Searching Authority dated Jan. 7, 2015 in PCT/EP14/72278 Filed Oct. 16, 2014.
(Continued)

*Primary Examiner* — Justine R Yu
*Assistant Examiner* — Matthew D Ziegler
(74) *Attorney, Agent, or Firm* — Oblon, McClelland, Maier & Neustadt, L.L.P.

(57) ABSTRACT

The system allows optimizing the dispensing of aerosol medicaments. In particular the system allows the administration of an exogenous pulmonary surfactant to very young patients (e.g. preterm neonates). A catheter (101) conveys atomized surfactant directly to the retropharyngeal region in order to increase efficiency of the medicament administration without being invasive: this is particularly important for very young patients, such as pre-term born neonates suffering from neonatal Respiratory Distress Syndrome (nRDS). The catheter is made of biocompatible flexible material (e.g.
(Continued)

Figure 1:
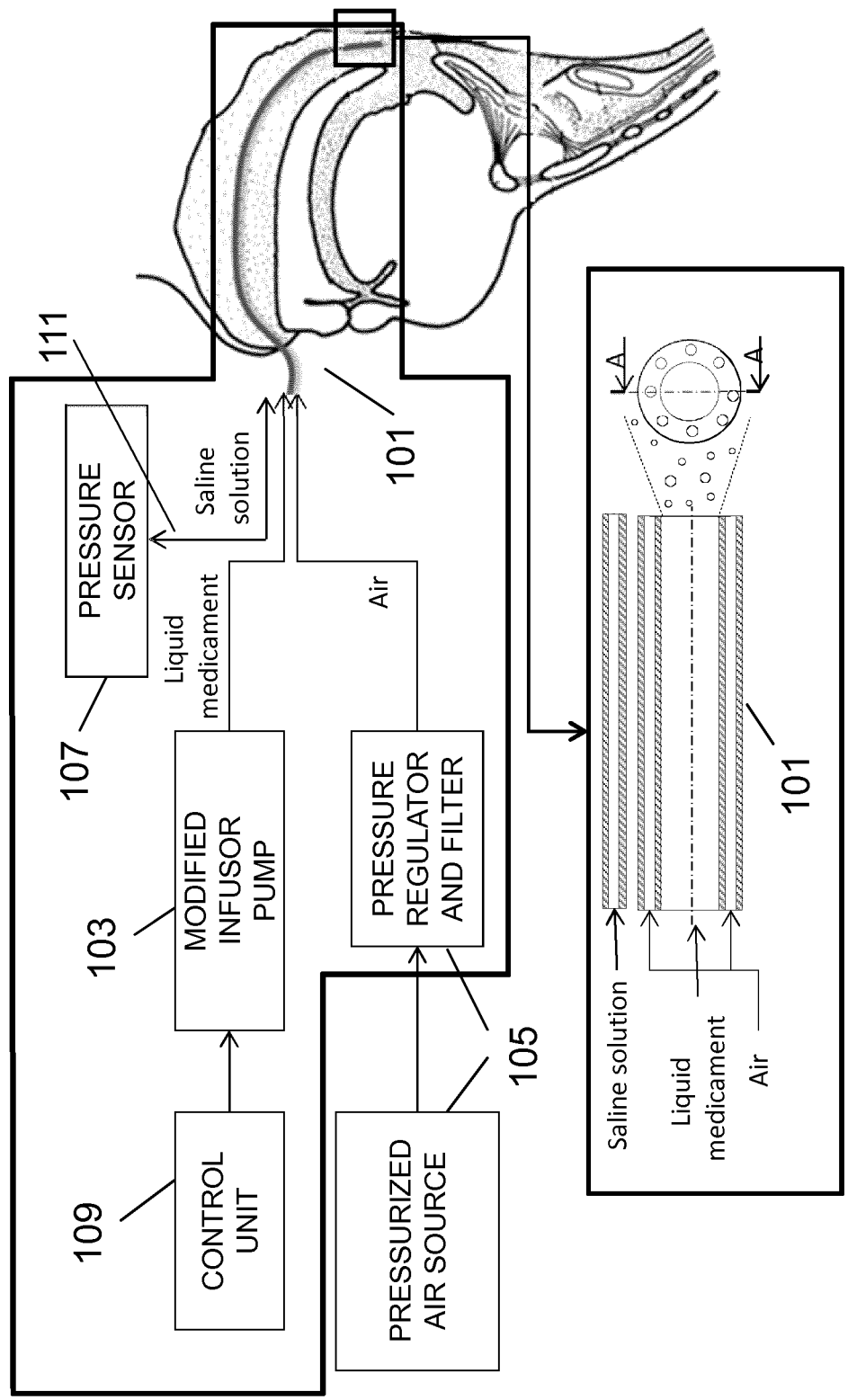
Figure 5A:
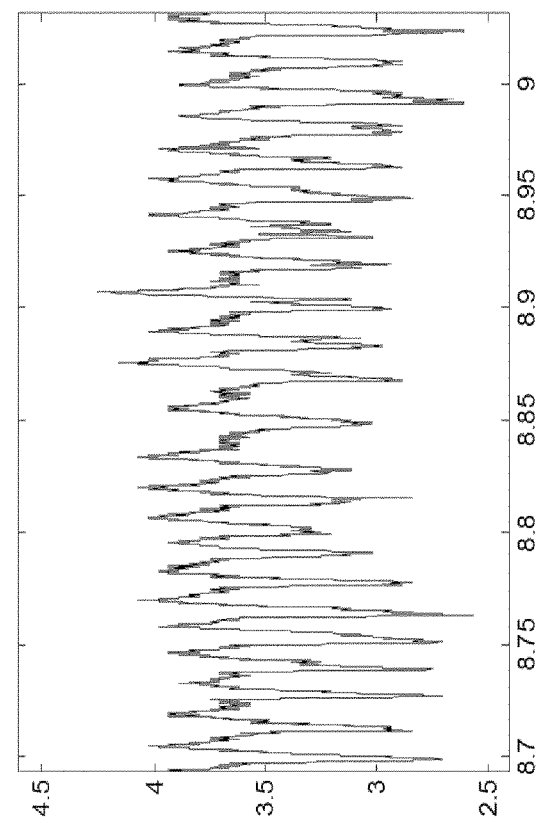
Figure 5B:
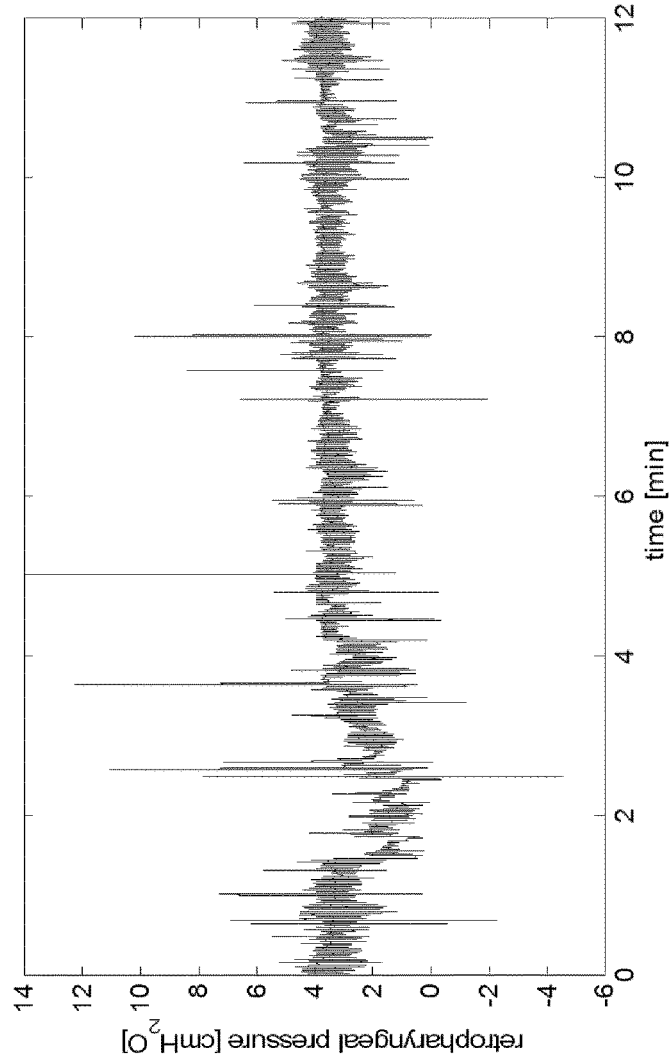
Figure 6:
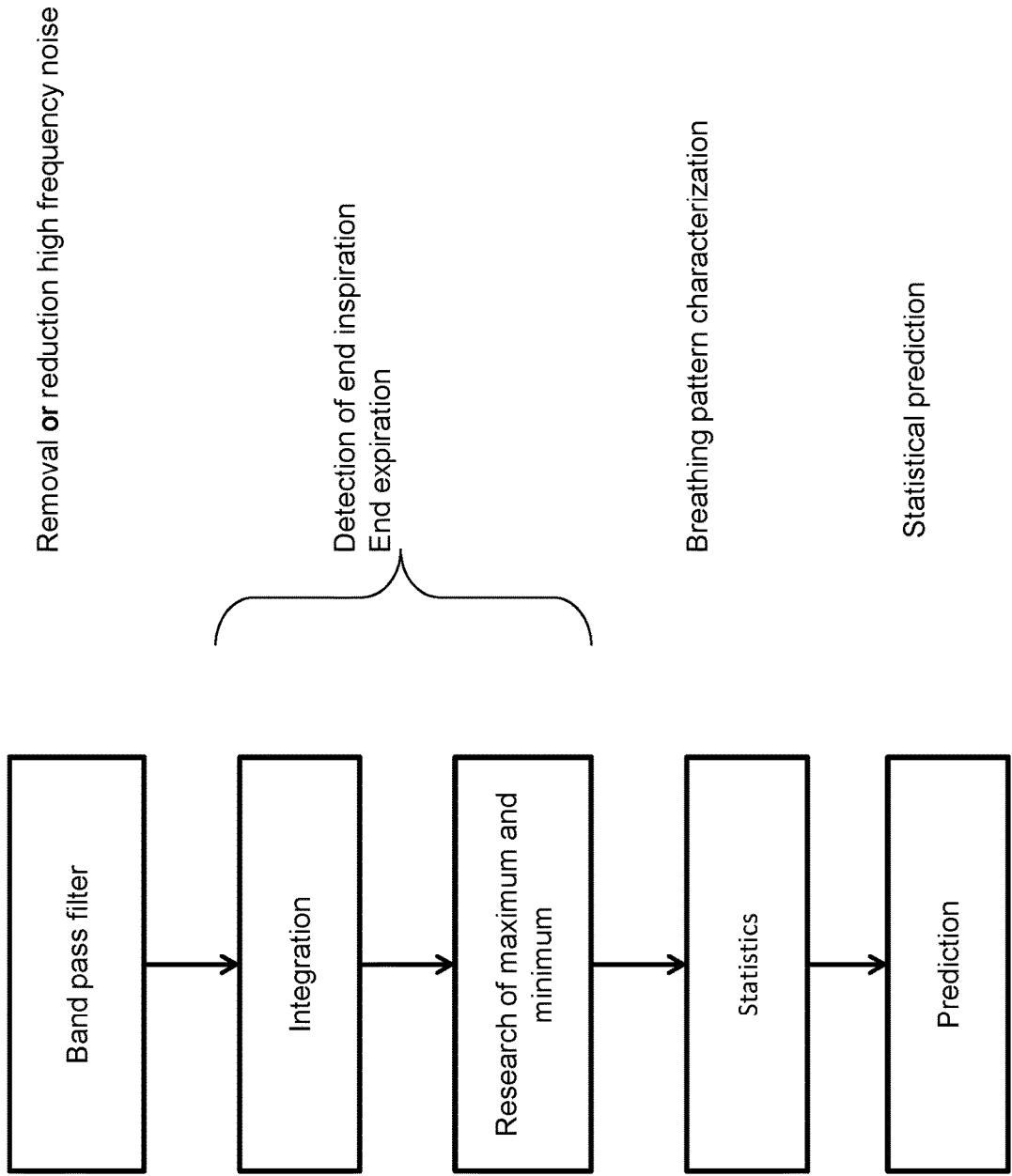

plastic material). It is possible to couple the catheter with a rigid scaffolding (e.g. metallic) to increase stiffness of the device and to improve easiness of positioning operations. The delivery of the atomized medicament is done by means of an air blasting technique.

9 Claims, 8 Drawing Sheets

(51) Int. Cl.
*A61M 16/14* (2006.01)
*A61M 16/06* (2006.01)
*A61M 25/00* (2006.01)

(52) U.S. Cl.
CPC ........ *A61M 16/14* (2013.01); *A61M 25/0026* (2013.01); *A61M 16/0488* (2013.01); *A61M 2025/0001* (2013.01); *A61M 2202/0488* (2013.01); *A61M 2210/065* (2013.01); *A61M 2210/1039* (2013.01); *A61M 2230/005* (2013.01); *A61M 2230/40* (2013.01); *A61M 2240/00* (2013.01)

(58) Field of Classification Search
CPC .............. A61M 16/00; A61M 16/0003; A61M 16/0057–0084; A61M 16/04; A61M 16/0461; A61M 16/0468; A61M 16/047; A61M 16/0475–0484; A61M 16/0486; A61M 16/0488; A61M 16/06; A61M 16/14; A61M 16/147; A61M 2016/0015; A61M 2016/0018; A61M 2016/0027; A61M 25/00; A61M 25/002; A61M 25/0026; A61M 2025/0001; A61M 2025/0003; A61M 2025/0004; A61M 2202/02; A61M 2202/0208; A61M 2202/0488; A61M 2210/065; A61M 2210/1039; A61M 2230/005; A61M 2230/40; A61M 2240/00; A61M 2039/082; A61M 2205/07; A61M 2209/06
See application file for complete search history.

(56) References Cited

U.S. PATENT DOCUMENTS

| | | | | |
|---|---|---|---|---|
| 4,621,646 A * | 11/1986 | Bryant | ................... | A61B 5/026 600/486 |
| 4,787,894 A * | 11/1988 | Turnbull | ........... | A61M 16/0486 604/319 |
| 4,813,431 A * | 3/1989 | Brown | ..................... | A61B 5/03 128/207.15 |
| 5,313,939 A | 5/1994 | Gonzalez | | |
| 5,803,080 A * | 9/1998 | Freitag | .................... | A61F 2/958 128/200.26 |
| 5,964,223 A | 10/1999 | Baran | | |
| 6,315,739 B1 * | 11/2001 | Merilainen | ......... | A61M 16/044 600/587 |
| 6,450,164 B1 * | 9/2002 | Banner | ................. | A61M 16/04 128/204.21 |
| 6,526,976 B1 | 3/2003 | Baran | | |
| 6,536,437 B1 * | 3/2003 | Dragisic | ............... | A61M 16/04 128/207.18 |
| 8,146,400 B2 * | 4/2012 | Goldfarb | ............. | A61B 1/0014 140/71 C |
| 8,701,658 B2 * | 4/2014 | Mazela | ............... | A61M 16/147 128/203.12 |
| 8,783,254 B2 * | 7/2014 | Bateman | ........... | A61M 16/0465 128/200.26 |
| 9,004,069 B2 * | 4/2015 | Efrati | .................. | A61M 16/044 128/207.15 |
| 2007/0197998 A1 * | 8/2007 | Itou | ..................... | A61M 25/002 604/523 |
| 2009/0107503 A1 | 4/2009 | Baran | | |
| 2009/0199848 A1 * | 8/2009 | Sharratt | ................ | A61M 31/00 128/200.14 |
| 2010/0089393 A1 | 4/2010 | Brain | | |
| 2011/0112469 A1 * | 5/2011 | Naqwi | ............... | A61B 17/3474 604/24 |
| 2011/0282268 A1 * | 11/2011 | Baker | ................... | A61M 15/08 604/20 |
| 2013/0030411 A1 * | 1/2013 | Kreck | ....................... | A61F 7/12 604/514 |
| 2013/0073015 A1 | 3/2013 | Rozenberg | | |
| 2013/0277443 A1 | 10/2013 | Croll et al. | | |
| 2013/0333695 A1 * | 12/2013 | Dellaca | .................. | A61B 5/036 128/200.14 |
| 2014/0000622 A1 * | 1/2014 | Azagury | ........... | A61M 16/0434 128/207.15 |

FOREIGN PATENT DOCUMENTS

| | | | | |
|---|---|---|---|---|
| GB | 2 444 779 A | | 6/2008 | |
| GB | 2444779 A | * | 6/2008 | ........... A61M 16/04 |
| WO | WO 01/23025 A1 | | 4/2001 | |
| WO | 2012/054013 A1 | | 4/2012 | |

OTHER PUBLICATIONS

Office Action dated Jun. 22, 2017 in European Patent Application No. 14784487.2, 6 pages.

* cited by examiner

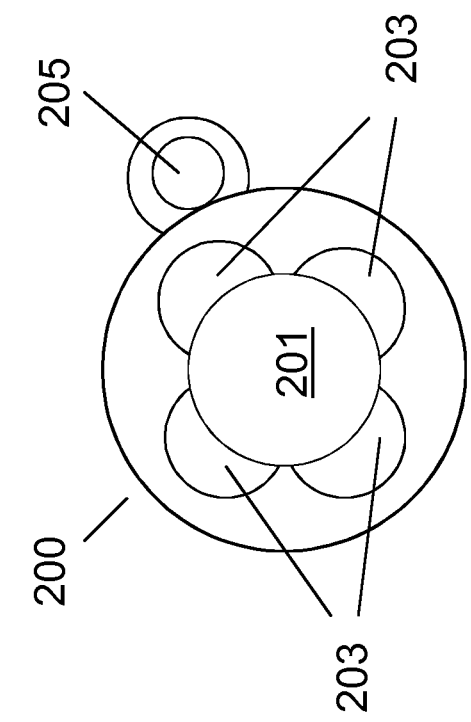
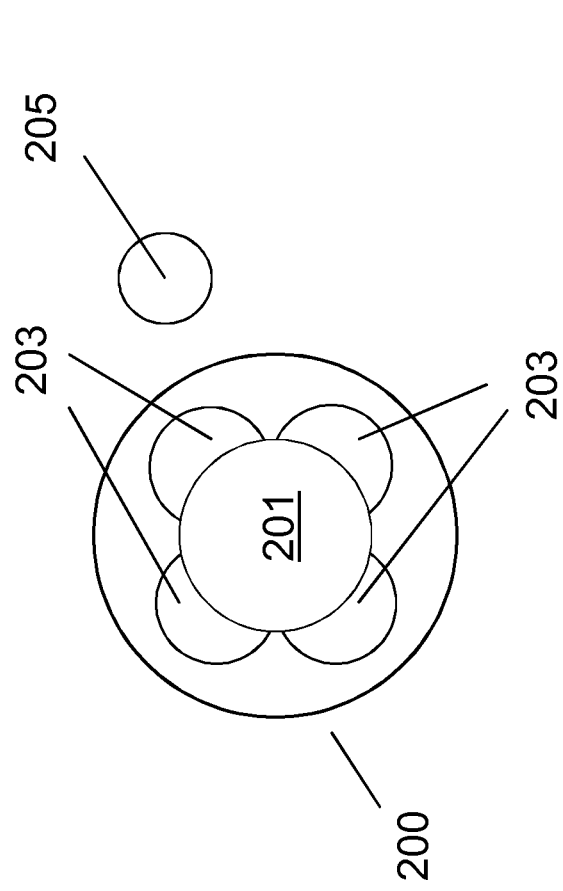
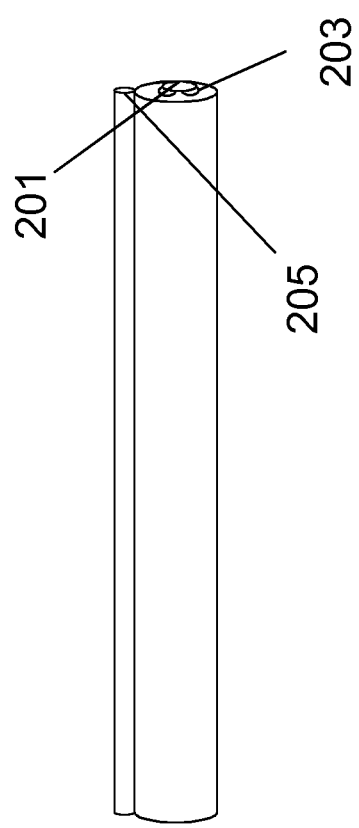
Fig. 2a
Fig. 2b

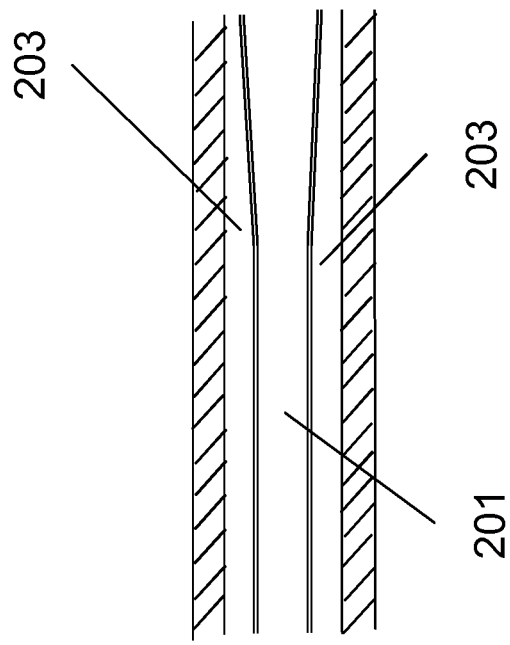
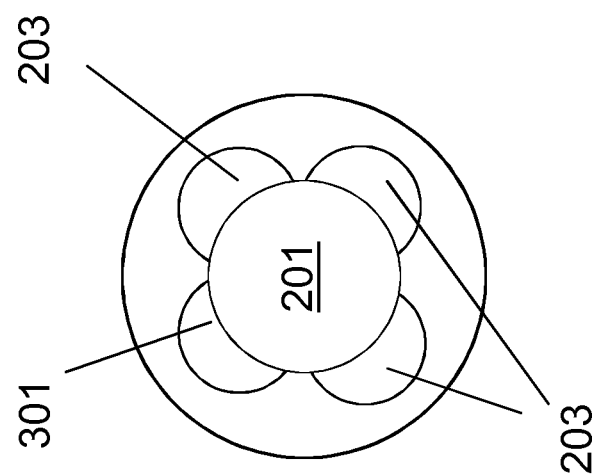
Fig. 3b
Fig. 3a

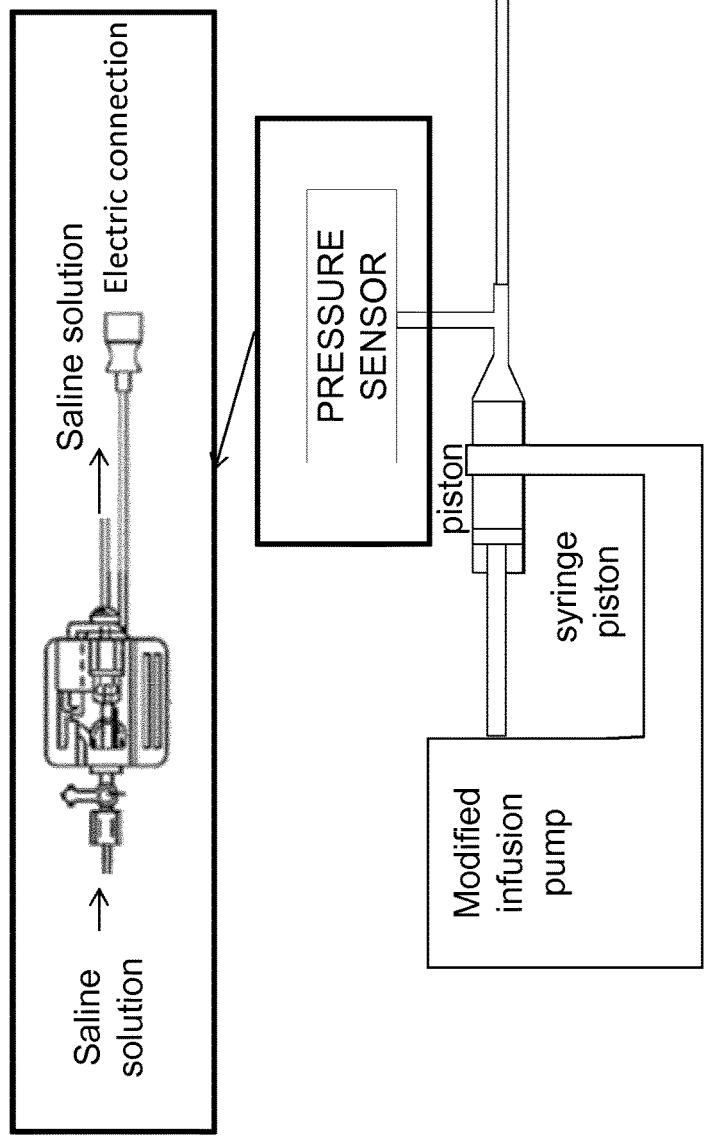
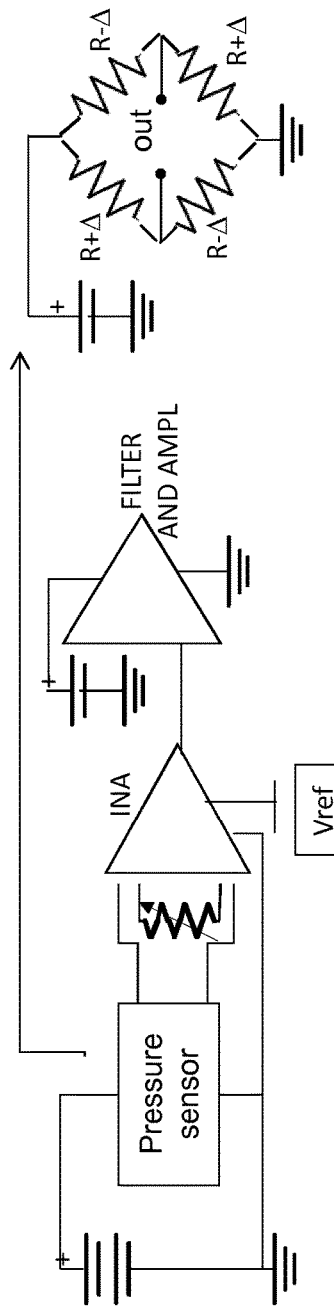
Fig. 4a
Fig. 4b

METHOD AND SYSTEM FOR THE ADMINISTRATION OF A PULMONARY SURFACTANT BY ATOMIZATION

CROSS REFERENCES TO RELATED APPLICATIONS

This application is a 371 of International Patent Application No. PCT/EP2014/072278, filed on Oct. 16, 2014, and claims priority to European Patent Application No. 13189768.8, filed on Oct. 22, 2013, both of which are incorporated herein by reference in their entireties.

FIELD OF TECHNOLOGY

The present invention relates to the field of retropharyngeal instillation of medicament and particularly to a method and system for the administration of a pulmonary surfactant by atomization.

BACKGROUND OF THE INVENTION

Administration of medicament in the lungs is often faced with the problem of finding the right balance between the efficacy and the invasiveness of the treatment. This is particularly difficult with infants (hereinafter the term neonates is used as synonymous of infants). Preterm neonates may be affected by nRDS (neonatal Respiratory Distress Syndrome), a lung disease due to generalized immaturity which causes the lack of pulmonary surfactant. For many years, nRDS has been treated by administration of exogenous pulmonary surfactants as bolus through endotracheal instillation to the intubated pre-term neonates kept under mechanical ventilation. Although this treatment is very effective, as proven by the reduced mortality, it may present some drawbacks which are intrinsic to the mechanical ventilation (volu/barotrauma) and to the intubation procedure which is anyway invasive.

In view of the potential complications associated with intubation and mechanical ventilation, attention has been focused on different approaches of administration of exogenous pulmonary surfactants.

In particular, as a possible respiratory support, use of non-invasive ventilation procedures such as early nasal Continuous Positive Airway Pressure (nCPAP), that delivers air into the lungs through specifically designed nasal devices such as masks, prongs or tubes, has been introduced in neonatal intensive care.

Following this orientation, in the last fifteen years great attention has also been paid to finding an alternative way for pulmonary surfactant administration. Most of the performed studies have been focused on the administration of nebulized surfactant (i.e. particles with a mass diameter <10 µm) by means of commercial nebulizers connected to the ventilator circuit, based on the hypothesis that a gentler and more gradual administration should prevent the high cerebral blood fluctuation that may occur with bolus administration (See e.g. Mazela J, Merrit T A, Finner N N "Aerosolized surfactants" Curr Opin Pediatr. 2007; 19(2): 155; or Mazela J, Polin R A "Aerosol delivery to ventilated newborn infants: Historical challenges and new directions" Eur J Pediatr. 2011:1-12; or Shah S "Exogenus surfactant: Intubated present, nebulized future?" World Journal of Pediatrics. 2011; 7(1): 11-5). Albeit the surfactant results more homogenously distributed, the improvements in the lung functionalities obtained in the different studies are very contrasting and they don't evidence the effectiveness of the nebulization approach. In other studies surfactant nebulization system was connected to non-invasive ventilator settings (i.e. CPAP through nasal prongs); in these conditions the amount of nebulized surfactant that reached the lung appeared to be negligible (less than 20%). Moreover nebulized surfactant administered during CPAP has no conclusive beneficial impacts on lung functionality as shown in pilot studies on preterm neonates (see e.g. Berggren E, Liljedhal M, Winbladh B, Andreasson B, Curstedt T, Robertson B, et al "Pilot study of nebulized surfactant therapy for neonatal respiratory distress syndrome" Acta Paediatrica 2000; 89 (4): 460-4; or Finner N N, Merritt T A, Bernstein G, Job L, Mazela J, Segal R "An open label, pilot study of Aerosurf combined with nCPAP to prevent RDS in preterm neonates" Journal of aerosol medicine and pulmonary drug delivery. 2010; 23(5): 303-9; or Jorch G, Hartl H, Roth B, Kribs A, Gortner L, Schaible T, et al "Surfactant aerosol treatment of respiratory distress syndrome in spontaneously breathing premature infants" Pediatr Pulmonol. 1997; 24(3):222-4). The studies are very variegated and the authors apply different conditions with reference to several parameters, e.g.: 1) placement and type of aerosol generator, 2) mode of ventilation, 3) humidity, 4) air flow, 5) particle size, 6) nRDS models, 7) surfactant dilution, etc.

Therefore it is difficult making a proper comparison among them. However known systems do not generally prove to be very effective.

Moreover, when an aerosolized surfactant is administered with a nebulizer through a mask and not synchronized with the neonate's breath, some part can be exhaled during expiration and either deposits into the upper airways or tubing/connections or it is exhaled by the expiratory limbs. Moreover, the delivery of nebulised surfactant adds deadspace to the breathing circuits and, considering that preterm newborns may have a tidal volume of 1 ml or even less, this can promotes $CO_2$ retention that, eventually, could become dangerous if a final situation of hypercapnia is achieved.

An interesting approach that could partially mitigate the above risk has been proposed by Wagner et al (Wagner M H, Amthauer H, Sonntag J, Drenk F, Eichstadt H W, Obladen M "Endotracheal surfactant atomization: an alternative to bolus instillation?" Crit Care Med. 2000; 28(7):2540) showing encouraging results. It is based on a modified tracheal tube with an atomizer inserted at the tip of the tube which produces particles, that have a SMD (Souter Mean Diameter) >100 µm, only during inspiration (identified by an operator). The choice of putting the atomizer directly into the tube has been technologically challenging.

The promising results of the Wagner approach are probably due to the rather large dimension of the particles which allow the distribution and absorption of the pulmonary surfactant similar to the mechanisms involved in the bolus administration. In particular, it can be hypothesized that big particles will deposit on more central airways, being able to reach the non-expanded alveoli by diffusion gradient, Marangoni effect and capillarity, while, on the contrary, the small nebulized particles, which are able to pass through the upper airways, are likely to be either exhaled during expiration or being deposited into the already opened alveoli which produces the airflow during breathing, without reaching the attelectatic region of the lung and contributing to an even more inhomogeneous distribution of lung time constants. Another advantage of Wagner is that the pulmonary surfactant is administered during inspiration phase only and this helps in better controlling the quantity of medicament effectively delivered, with improvements in terms of saving and clinical results.

A drawback of Wagner is that the tube must reach the trachea (where the nebulizer is placed), in order to be able of delivering the rather large sized particles which would be filtered out by the upper airways, and this procedure is invasive and can cause problems, in particular for neonates. On the other hand, all known prior art systems implementing a non-invasive (i.e. not entering the tracheal tube) delivery method are capable of administering only small sized particles which are able to overcome the outer barrier, but are less efficient in reaching all the lung regions needing treatment.

Furthermore, according to Wagner experiment, the "synchronization" of the delivery of medicament with the inspiration rhythm is done manually, which is not ideal for obvious reasons including a waste of the product. On the other hand all attempts known in the art for implementing such synchronization, for example those described in EP 692273, are depending on the presence of devices such as a mechanical ventilator. However, this solution needs connections to the airway of the newborn, adding dead space and mechanical load to the patient's breathing. For all these reasons, an improved non-invasive method and system for administering the exogenous surfactant which is capable of partly combining the advantages of Wagner et al with proper automatic synchronization of the delivery would be greatly appreciated.

OBJECTS OF THE INVENTION

It is an object of the present invention to overcome at least some of the problems associated with the prior art.

SUMMARY OF THE INVENTION

The present invention provides a method and system as set out in the accompanying claims.

According to one aspect of the present invention, we provide a system for delivering a medicament comprising a pulmonary surfactant to spontaneously breathing patients, comprising: i) a catheter adapted to reach the retro-pharyngeal region of the patient, the catheter including at least a first channel being adapted to convey in the patient's pharyngeal region a flow of liquid medicament and at least a second channel adapted to convey in the patient's pharyngeal region a pressurized flow of gas, ii) first pump means connected to a first end of the at least first channel, adapted to create a pressure which pushes the column of liquid medicament towards the second end of the at least first channel;

iii) second pump means connected to a first end of the at least second channel, adapted to create the flow of pressurized gas, so that when the column of liquid medicament and the pressurized gas meet in the pharyngeal cavity, the liquid column is broken into a plurality of particles causing the atomized medicament to be delivered into the patient's lungs;—iv) pressure detecting means, separate from the first and second channel for measuring a value indicative of the pressure in the patient pharyngeal cavity, such value being used to determine whether the patient is in an inspiration or in an expiration phase and wherein the first pump means are selectively activated only during inspiration phase.

In a preferred embodiment the breathing activity is assessed by measuring the pressure swings in the retropharyngeal cavity; in a more preferred embodiment the pressure detecting means include: a third channel adapted to convey in the patients pharyngeal region a flow of a water solution; third pump means to create a constant flow of water solution; and a pressure sensor connected to the third channel for measuring a value indicative of the pressure on the flow of water solution.

The use of a liquid-filled lumen (embedded in the catheter assembly or completely separate from it) for estimating the pressure swings at the pharyngeal cavity allows specific advantages compared to other approaches: 1) it provides a very fast response of the catheter-pressure transducer system (liquids are not compressible and adds a minimal compliance of the measuring system, resulting in very fast time constants), allowing a prompt detection of the newborns breathing phase (respiratory rate in small preterm neonates can be greater than 60 breaths per minute, one order of magnitude greater than for adults); 2) the presence of liquid in the lumen prevents the tip of the catheter to be occluded by the fluids always present in the pharynx, for example saliva or moist due to the water vapor saturated environment, an important advantage against air-filled lumens for pressure sensing.

Preferably the catheter is made of flexible plastic material and as an alternative it can include partially rigid scaffolding. Preferably the at least second channel includes a plurality of channel arranged around the first channel. In a preferred embodiment the third channel is embedded within the catheter assembly. In a particular embodiment, the third channel is one of those around the first channel.

Preferably, the aerosol medicament comprises an exogenous pulmonary surfactant, e.g. selected from the group consisting of modified natural pulmonary surfactants (e.g. poractant alfa), artificial surfactants, and reconstituted surfactants.

Also, in a preferred embodiment, the pressurized gas includes air or oxygen.

According to a further embodiment the catheter includes spacers means arranged on its external surface so that, when the catheter is in place for the aerosol treatment, the second end of the at least first and at least second channel are kept separated from the wall of the pharyngeal cavity.

In a second aspect of the invention, we provide a method for preventing and/or treating a respiratory distress syndrome in spontaneously breathing patients, said method comprising the step of delivering an atomized medicament to the retro-pharyngeal region of the patient by means of a multi-channel flexible catheter a low pressure column of liquid medicament through at least a first channel of the multi-channel catheter and an pressurized flow of gas through at least a second channel of the multi-channel catheter; wherein the liquid column of medicament is broken into a plurality of particles when the liquid column and the pressurized flow of gas meet in the retro-pharyngeal cavity; the inspiration activity of the patient is detected by means of a pressure sensor e.g. connected to at least a third channel adapted to convey a flow of water solution in the retro-pharyngeal region; wherein the step of providing is performed only during the inspiration activity. In a preferred embodiment the water solution is a physiological saline (0.9% w/v sodium chloride) aqueous solution, optionally buffered at a physiological pH.

More preferably, the method of the invention comprises applying to the patient a non-invasive ventilation procedure such as nasal Continuous Positive Airway Pressure (nCPAP).

In a third aspect of the invention, we provide a kit comprising: a) a pharmaceutical composition comprising a pulmonary surfactant suspended in a pharmaceutically acceptable aqueous medium; b) the system of the invention; c) means for positioning and/or facilitating the introduction of the catheter into the retro-pharyngeal region; and d) container means for containing the pharmaceutical composition, the system and the positioning means. In a certain embodiment of the present invention the means for positioning include a laryngeal mask. In a fourth aspect of the invention, we provide a method for preventing and/or treating a respiratory distress syndrome in spontaneously breathing pre-term neonates, said method comprising the step of delivering a pulmonary surfactant in the retro-pharyngeal cavity of said neonates only during the inspiration phase which is detected by means of a pressure sensor. A still further aspect of the present invention provides a computer program for controlling the above described method.

The method and system according to preferred embodiments of the present invention allows optimizing the dispensing of surfactant with an efficient delivery of the atomized particles to the lungs without requiring an invasive operation for placing the catheter. The method and system of the present invention provides several advantages including: a more gentle atomizing process, thanks to the air-blasting atomizing catheter, whose mechanical impact on the surfactant is minimal; the possibility to monitor and to synchronize to the breathing pattern of the patient without the introduction of a sensor, connections at the airway opening or a second lumen; the flexibility of the device, which can be used either during spontaneous breathing or when non-invasive respiratory support is provided, such as during nCPAP or other non-invasive ventilation procedures such as nasal intermittent positive-pressure ventilation (NIPPV); the use of components which are already familiar to the hospital personnel, e.g. catheters and disposable pressure sensors (similar to the ones used for invasive monitoring of blood pressures); all the part in contact with the pulmonary surfactant and the patient are low cost and disposable, granting for hygienically and safer treatments than those of the prior art, which is particularly important when the patient is a pre-term neonate.

BRIEF DESCRIPTION OF THE DRAWINGS

Reference will now be made, by way of example, to the accompanying drawings, in which:

FIG. 1 is a schematic diagram of the system implementing a preferred embodiment of the present invention;

FIG. 2 shows two examples of catheter assembly according to an embodiment of the present invention, including multi lumen catheter and a third channel for measuring the retro-pharyngeal pressure FIG. 3 shows as example of a particular shape of channels in a multi-lumen catheter according to an embodiment of the present invention;

FIGS. 4*a* and 4*b* represent respectively a pressure sensor according to an embodiment of the present invention and the circuit controlling the pressure sensor;

FIG. 5 shows an exemplificative retropharyngeal pressure signal acquired on a preterm neonate.

FIG. 6 shows the steps of the method according to a preferred embodiment of the present invention;

FIG. 7 shows a diagram of tidal volume related to fetuses being treated with the method and system according to an embodiment of the present invention;

FIG. 8 shows the effects of atomized surfactant on the alveolar-arterial oxygen concentration ratio (ΔaA Ratio). Open circles: atomized lambs; closed diamonds: CPAP control group. Oxygenation was measured for 105 minutes from birth. Since the baseline values of aA Ratio is highly variable, data reports changes from baseline. The atomization group demonstrated a statistically better change in aA ratio at 90 and 105 min from birth ($p<0.05$ and $p<0.001$, respectively, 2-way ANOVA with Sidak post tests), compared to CPAP group.

DEFINITIONS

With the term "pulmonary surfactant" it is meant an exogenous pulmonary surfactant administered to the lungs that could belong to one of the following classes:

i) "modified natural" pulmonary surfactants which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta™ are spiked with synthetic components such as tripalmitin, dipalmitoylphosphatidylcholine and palmitic acid.

ii) "artificial" pulmonary surfactants which are simply mixtures of synthetic compounds, primarily phospholipids and other lipids that are formulated to mimic the lipid composition and behavior of natural pulmonary surfactant. They are devoid of pulmonary surfactant proteins;

iii) "reconstituted" pulmonary surfactants which are artificial pulmonary surfactants to which have been added pulmonary surfactant proteins/peptides isolated from animals or proteins/peptides manufactured through recombinant technology such as those described in WO 95/32992 or synthetic pulmonary surfactant protein analogues such as those described in WO 89/06657, WO 92/22315, and WO 00/47623.

The term "non-invasive ventilation (NIV) procedure defines a ventilation modality that supports breathing without the need for intubation.

DETAILED DESCRIPTION OF PREFERRED EMBODIMENTS

With reference to FIG. 1 an implementation of the method and system according to a preferred embodiment of the present invention is illustrated. In the example here discussed we address the problem of delivering the right amount of atomized medicament to a patient: in particular we administrate a pulmonary surfactant (e.g. poractant alfa, commercially available as Curosurf® from Chiesi Farmaceutici SpA) to e.g. a preterm neonate.

However, any pulmonary surfactant currently in use, or hereafter developed for use in respiratory distress system and other pulmonary conditions could be suitable for use in the present invention. These include modified natural, artificial and reconstituted pulmonary surfactants (PS).

Current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), poractant alfa (Curosurf™, Chiesi Farmaceutici SpA, Parma, Italy), and beractant (Survanta™, Abbott Laboratories, Inc., Abbott Park, Ill.)

Examples of artificial surfactants include, but are not limited to, pumactant (Alec™, Britannia Pharmaceuticals, UK), and colfosceril palmitate (Exosurf™, GlaxoSmithKline, plc, Middlesex).

Examples of reconstituted surfactants include, but are not limited to, lucinactant (Surfaxin™, Discovery Laboratories, Inc., Warrington, Pa.) and the product having the composition disclosed in Table 2 of Example 2 of WO 2010/139442, whose teaching is incorporated herein by reference.

Preferably, the pulmonary surfactant is a modified natural surfactant or a reconstituted surfactant. More preferably the pulmonary surfactant is poractant alfa (Curosurf®). In another preferred embodiment, the reconstituted surfactant has composition disclosed in WO 2010/139442 (see Table 2 of Example 2). The dose of the pulmonary surfactant to be administered varies with the size and age of the patient, as well as with the severity of the patient's condition. Those of skill in the relevant art will be readily able to determine these factors and to adjust the dosage accordingly.

Other active ingredients could advantageously be comprised in the medicament according to the invention including small chemical entities, macromolecules such as proteins, peptides, oligopeptides, polypeptides, polyamino acids nucleic acid, polynucleotides, oligo-nucleotides and high molecular weight polysaccharides, and mesenchimal stem cells derived from any tissue, in particular from a neonate tissue. In a particular embodiment, small chemical entities include those currently used for the prevention and/or treatment of neonatal respiratory diseases, for example inhaled corticosteroids such as beclometasone dipropionate and budesonide.

A catheter 101 conveys atomized medicament (e.g. surfactant) directly to the retro-pharyngeal region in order to increase efficiency of the medicament administration without being invasive: this is particularly important for very young patients, such as pre-term born neonate suffering from neonatal Respiratory Distress Syndrome (nRDS). According to a preferred embodiment of the present invention the catheter is made of biocompatible flexible material (e.g. plastic material). It is possible to couple the catheter with a rigid scaffolding (e.g. metallic) to increase stiffness of the device and to improve easiness of positioning operations. In a preferred embodiment of the present invention the delivery of the atomized medicament is done by means of an air blasting technique. Using air to assist atomization is a well-known technique that grants a fully developed atomization also when low pressure and low flow conditions are required (see e.g. Arthur Lefebvre, "Atomization and spray", Taylor and Francis, 1989). Such technique is based on a relatively small amount of gas (e.g. air, but it could be other compressed gas, e.g. oxygen, nitrogen, or helium) which flows in one or more separate channels than the medicament which is delivered in a liquid form; the air flow accelerates and breaks the liquid column, inducing the atomization of the medicament. Therefore the multi-lumen catheter 101 includes a plurality of channels (at least two, one for the medicament and one for the air) for conveying contemporarily the medicament and the air flow. The liquid medicament column is broken up in droplets by the turbulence due to the air flowing next or around when the two flows (air and liquid medicament) exit the catheter channels and meet in the retro-pharyngeal region. The atomized droplets have a median diameter of at least 20 micron, preferably equal to or higher than 40 micron, more preferably equal to or higher than 60 micron. It is believed that this effect is caused by the air flow which accelerates the fluid sheet instability. The air also helps in dispersing the droplets, preventing collision among them and facilitating the diffusion of the medicament in the lungs by reducing the likelihood of contact between the particles and the wall of the retropharyngeal cavity. In a preferred embodiment the cross section of the air ducts decreases in proximity of the exit, as shown in FIG. 3. According to Poiseuille law, the flow resistance is increasing linearly with the length of the catheter and inversely proportional to the fourth power of the radius of the lumen. Therefore, by using a catheter with a greater lumen for most of its total length, the total resistance of the air pathway is drastically lowered causing a reduction in the pressure applied to the entrance of the catheter needed to atomize the drug.

In a certain embodiment of the invention it is possible to shape the air ducts in order to modify not just the velocity, but the direction of the gas flow as well. For instance it is possible to have wings shape ducts that can model the ejection angle.

In a preferred embodiment of the present invention the medicament (e.g. the surfactant) is supplied by means of a pump 103 connected to one end of the catheter, which forces the liquid medicament out of the opposite end of the catheter where it meets the air flow (conveyed by a different channel of the catheter) and is atomized, i.e. broken into a plurality of small particles (droplets) by the pressurized air. Pump 103 may be realized by a device able to generate a flow, such as an infusion pump: in a preferred embodiment of the present invention, the pump 103 is made of a mechanical frame comprising a structure that holds a syringe containing the liquid medicament and a stepper motor that pushes the syringe piston. In an embodiment of the present invention, pump 103 can be controlled by a control unit 109; such control unit can be embodied in a computer, a microprocessor or, more generally any device capable of data processing activity. A pump device 105 (possibly including a pressurized source and pressure regulator and filter) is connected to the one or more channel conveying the air flow. Those skilled in the art will appreciate that with the term pump we include any device capable of providing a pressure to either a liquid flow or a flow of gas. Pump 105 can be controlled by a control unit, as described for the pump 103. The flow of the pump 103 should be in the range of 9-18 ml/H while the flow of the pump 105 should be less than 1 L/minute, in a preferred embodiment less than 0.75 L/min in order not to interfere with any spontaneous or aided breathing activity.

In a preferred embodiment of the present disclosure the catheter 101 includes multiple channels, with a main (e.g. central) channel conveying the surfactant, being surrounded by a plurality of additional channels (e.g. lateral) which convey a pressurized air flow). The air blasting technique here described provides the advantage of a more gentle fragmentation of the surfactant. Current atomizers for drug delivery are normally based on orifices, while the method according to the present disclosure employs an atomizing catheter using the air blasting approach. The geometrical configuration of the plain orifice normally presents a narrowing at the tip of the catheter, the nozzle, which accelerates the liquid producing an high instability in presence of an high pressure drop (more than 1 Atm) and, as a consequence, the fragmentation of the liquid in particles. On the contrary, the air blasting catheter according to a preferred embodiment of the present disclosure is a multi-lumen catheter: the surfactant flows into the main lumen while pressurized air flows in the lateral ones. The turbulences generated by the small airflow fragment the surfactant in a very 'gentle' way. Moreover, the use of plain orifices would require very high differential pressure across the nozzle to induce atomization, while the air blasting atomizer doesn't need high driving pressure to the surfactant, as the atomizing process is driven by the turbulence of the air around the surfactant.

The pulmonary surfactant is preferably administered as a suspension in a sterile pharmaceutically acceptable aqueous medium, preferably in a buffered physiological saline (0.9% w/v sodium chloride) aqueous solution.

Its concentration shall be properly adjusted by the skilled person in the art.

Advantageously, the concentration of the surfactant might be comprised between 2 and 160 mg/ml, preferably between 10 and 100 mg/ml, more preferably between 40 and 80 mg/ml.

The applied volume should generally be not more than 5.0 ml, preferably not more than 3.0 ml. In some embodiments, it could be 1.5 ml or 3 ml.

The pulmonary surfactant administration is synchronized with the breathing phase of the patient. To implement this feature, sensing means of any variable related to the breathing activity must be implemented for an indirect but accurate measurement of the inspiratory phases. Possible embodiments of such pressure sensing means include the usage of micro pressure sensor at the tip of the catheter, respiratory inductance pletysmography, fiber optic pressure sensor. According to a preferred embodiment of the present invention the pressure sensing means include a dedicated channel 111 (a third channel, e.g. a catheter, different from the first at least one channel conveying surfactant medicament and from the at least second channel conveying air for air-blasting effect) which conveys a flow of water solution, e.g. a physiological saline (0.9% w/v sodium chloride) aqueous solution, optionally buffered at a physiological pH, according to conditions well-known to the skilled person in the art. As shown in FIG. 1, a pressure sensor 107 monitors the breathing rhythm by sensing the pressure on the column of saline solution in the retro/pharyngeal region. Not shown in FIG. 1 the system according a preferred embodiment of the present invention also includes (third) pump means (possibly including a pressurized source and pressure regulator and filter) connected to the third channel conveying the water solution. Those skilled in the art will appreciate that with the term pump we include any device capable of providing a constant flow of liquid. This third pump can be controlled by a control unit, as described for the pump 103 and 105. Preferably the flow of the third pump shall be in the range of 0.1-10 ml/hour in order to avoid to add too much liquid into the pharynx during the delivery of the surfactant.

Two possible embodiments for the catheter assembly 200 are shown in FIG. 2: in particular FIG. 2a shows two views (a section view and a longitudinal view) of a catheter assembly according to an embodiment of the present invention, with the third channel 205 completely separate from the multi-lumen catheter, including medicament lumen 201 and a plurality of air lumens 203; while FIG. 2b shows similar views of an embodiment where the third channel is attached to the multi-lumen catheter. In a preferred embodiment the cross section of central medicament lumen is comprised 0.25 and 0.5 mm while air lumens should have a cross section between 0.05 and 0.15 mm, where the ratio of surfactant to air lumen areas should be comprised between 0.2 and 2, considering the cumulative cross-sectional area of the respective lumen at the catheter tip.

A pressure sensor is coupled to the third channel and inserted along the water solution catheter. This measurement is possible because of the relatively low pressure in the channel conveying the water solution, allowing the use of water solution un-interrupted column for measuring the retro-pharyngeal pressure with the aim of both synchronizing the atomization with the breathing pattern of the patients and to help the attending medical staff to place the catheter in the proper place and monitoring the maintenance of the proper position during the treatment, allowing the identification of wrong positioning of the catheter tip (e.g. into the oesophagus). As mentioned above, a pump (third pump means) ensure the maintenance of a constant liquid flow to avoid occlusions at the opening of the third channel.

As mentioned above, FIG. 2 shows a specific implementation of the multi-channel catheter according to a preferred embodiment of the present invention. The air blasting atomizer of the present embodiment is realized by means of a multi-lumen catheter with a central inner lumen 201 surrounded by several smaller lumens 203. The surfactant flows into the main central lumen, driven by the infusion pump, while the gas (e.g. air, oxygen-enriched air or pure oxygen), flows through the lateral lumens. The pressure drop in the central catheter depends on its length and internal diameter. In a preferred embodiment of the present disclosure the catheter could present a length of 7-15 cm and an internal diameter of 0.6-0.8 mm. According to a preferred embodiment the surfactant lumen has a diameter of 0.75 mm, while the lateral lumen for gas may be a single lumen for all the length of the catheter except for the 5 distal millimetres at the tip, where it can change its shape into a plurality of lumens coaxial to the surfactant lumen. This solution allows reducing the total resistance of the gas lumen lowering the gas pressure needed to atomize, moreover the velocity of the gas is increased helping the atomization process. In this case the pressure drop is in the range of 3.5-8 $cmH_2O$, considering a flow of surfactant of 3 mL/20 min. In this way a nozzle is not required and the particles size dimension is determined mainly by the flow of the air which flows in the lateral channel. To generate the gas flow into the lateral lumens a compressor or a pressurized gas source (e.g. a cylinder or a medical gas wall plug) can be used: the pressure is modulated by a pressure regulator with a mechanical filter to avoid dust flowing through the system.

Such pressurized gas flow is not able to significantly alter the pressure in the pharynx, since the flow is rather limited and the anatomical structures are open to the atmosphere: in a preferred embodiment the flow is equal or lower than, 1 L/min.

FIG. 3a shows a possible embodiment of the catheter, where the third channel (conveying the water solution) 301 is one of those around the first (central) one 201; Channel 301 and channels 203 are all placed around the central one with channels 203 conveying the pressurized air and the channel 301 conveying the water solution.

FIG. 3b shows an optional feature of the catheter assembly of present invention, with the air lumens 203 having a section which decreases towards the exit. FIG. 3b shows a longitudinal section view. In a preferred embodiment such decrease in the section of air lumens is caused by a corresponding enlargement of the central medicament-carrying lumen 201. The embodiment shown in FIG. 3b is just one of the possible option to implement such features: as a possible alternative the external walls of the multi-lumen catheter can become thicker towards the end, so that the air lumens are restricted; another possible implementation could be that of decreasing the total section of the multi-lumen catheter, maintaining the size of the central channel (lumen) unchanged.

The distribution of the particles size obtained by means of the preferred embodiment of the present invention has been characterized by a commercial laser diffractive size analyzer (Malvern, Insitec RT). The measurements have been carried out using exemplificative conditions of 0.75 bar of pressurized air; flow rate of the surfactant in the condition of use (from 9 mL/H to 1.2 mL/min) not affect the dimension of particles As a result the most of the particles size is comprised between 20 and 100 micron.

As a possible additional feature the catheter used in the method and system of the present disclosure could be provided with some spacers on the external surface which help in positioning it and keeping a minimum distance between the catheter itself and the wall of the retro-pharyngeal cavity. This separation ensures that the atomised surfactant is conveyed to the lung by inspiratory airflow and not projected on the walls of the pharyngeal cavity. An example is shown in FIG. 2*b* where some ribs are running along the external surface of the catheter; these ribs can also have a stiffening function adding some sort of rigidity to the catheter (as an alternative to the metal scaffolding mentioned above). Other shapes of the ribs are possible, e.g. they could be in the shape of one or more rings surrounding the catheter at predetermined distance one each other: those skilled in the art will appreciate that several equivalent alternatives can be implemented.

Laryngoscope is another tool known to the skilled person, that could be suitably utilized for positioning the catheter in the retro-pharyngeal cavity.

Moreover, Magill forceps, oro-pharyngeal cannulas such as cannula of Mayo, of Guedel, of Safar and of Bierman, and laryngeal mask could facilitate the introduction of the catheter. In a certain embodiment the cannula of Mayo is utilised for both facilitating the introduction and keeping the catheter tip in the proper position, i.e. not close to the pharyngeal wall and pointing toward the inlet of the trachea during the whole period of surfactant delivery. In another embodiment, the laryngeal mask may be used.

The third channel, as mentioned above, must be kept separate from the at least first channel carrying the surfactant medicament and from the at least second channel conveying air flow, because measuring the pressure too close to the air-blasting area can bring to inaccurate measures, however several possible solution are available, including keeping the third channel completely separate or connecting the third channel in some ways with the other two. It could be possible to design the catheter assembly to include the third channel, creating a separation between the exit of the third channel and the exit of the medicament and air channels. Another possible implementation is that of embedding the water solution carrying channel (the third channel) within the positioning tool, e.g. the Mayo cannula. FIG. 4*a* shows a possible implementation of the pressure sensor 107 mentioned above, which is used in an embodiment of the present invention to detect the pressure of the air coming from or flowing into the pharyngeal cavity. Such measured pressure is used as an indication of the breathing rhythm of the patient and the system synchronizes the administration of the medicament accordingly. This synchronization brings big advantages both in term of efficacy of the treatment and in reducing the waste of medicament. The efficacy is due to the transportation of the atomized drug by the inspiratory flow; the saving is caused by the fact that the medicament is delivered only when needed, avoiding to waste it while the patient is exhaling. In an embodiment of the present disclosure the pressure sensor is inserted along the water solution line (the third channel) and transduces the pressure from the tip of the catheter (i.e. the pressure in the neonate pharynx) to the sensing element which acts as a variable resistance. When the motor is activated the syringe gently pushes the surfactant into the atomizing catheter to allow an averaged flow between 0.5 and 3 ml/h, preferably 2.4 ml/h (this parameter can be adjusted on the treatment program). The water solution flow in the third channel can be as low as needed to prevent from mucus adhesion, e.g. 1 ml/h. As shown in FIG. 4*b*, the sensor exploits the piezoresistive phenomenon to convert the mechanical pressure into a voltage drop; it has an internal Wheatstone Bridge connection, which means that it is internally compensated for ambient temperature fluctuations.

The sensor can be for example a disposable pressure sensor, similar to those used for the invasive measurement of blood pressure.

The administration of surfactant only during the inspiration phase is a big advantage provided by the present invention: this results in a better control on the effective quantity which reaches alveoli and to avoid the waste of the supplied surfactant. This requires the measurement of a signal related to the breathing pattern in the ventilatory condition of the preterm neonate (spontaneously breathing and kept under nCPAP or other non-invasive ventilation procedure such as NIPPV) to detect the end-inspiration and end-expiration and to predict the 'future' breathing pattern of the baby. According to an embodiment of the present invention, we start the administration of surfactant before the beginning of the inspiration and stop it before the beginning of the expiration in order to:

1) Take into account the mechanical delays in the atomization;

2) Prevent the loss of surfactant since the surfactant delivered at end inspiration will be still in the pharyngeal cavity and therefore exhaled during the beginning of the expiration.

In FIG. 5 are reported retropharyngeal pressure tracings from a representative preterm baby with gestational age of 28 weeks and a body weight of 1650 g. Panel a shows the whole track characterized by a very high variability with several spikes and base line fluctuations; in panel b an enlargement of the same signal is reported. A statistical analysis on the data has been performed and a predictive algorithm has been designed. The main steps of which are reported in the flow chart of FIG. 6, with the relative functions. In particular, after the removal of trends and high frequency noise, the signal is integrated to obtain a new signal proportional to the lung volume, and by looking for maxima and minima it is possible to detect the end-inspiratory and end-expiratory points. Our statistical analysis includes also the measurement of the pressure involved, which is about 1 $cmH_2O$ in all the different conditions.

By using this approach we have obtained in an exemplificative simulation, the administration of the 97±0.8% of surfactant in 60±21 min in 7 preterm neonates with a gestational age of 29.5±3 weeks and a body weight of 1614 g (±424 g).

All operations of the system here described are controlled by a microprocessor (e.g. microcontroller of PIC 18F family by Microchip Technology Inc. or more advanced versions) running a software adapted to implement the method according to a preferred embodiment of the present invention.

It will be appreciated that alterations and modifications may be made to the above without departing from the scope of the disclosure. Naturally, in order to satisfy local and specific requirements, a person skilled in the art may apply to the solution described above many modifications and alterations. Particularly, although the present disclosure has been described with a deep degree of particularity with reference to preferred embodiment(s) thereof, it should be understood that eventual omissions, substitutions and changes in the form and details as well as other embodiments are possible; moreover, it is expressly intended that specific elements and/or method steps described in connection with any disclosed embodiment of the disclosure may be incorporated in any other embodiment as a general matter of design choice.

For example, similar considerations apply if the components (e.g. microprocessor or computers) have different structure or include equivalent units; in any case, it is possible to replace the computers with any code execution entity (such as a PDA, a mobile phone, and the like).

Similar considerations apply if the program (which may be used to implement some embodiments of the disclosure) is structured in a different way, or if additional modules or functions are provided; likewise, the memory structures may be of other types, or may be replaced with equivalent entities (not necessarily consisting of physical storage media). Moreover, the proposed solution lends itself to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium can be any element suitable to contain, store, communicate, propagate, or transfer the program. Examples of such medium are fixed disks (where the program can be pre-loaded), removable disks, tapes, cards, wires, fibres, wireless connections, networks, broadcast waves, and the like; for example, the medium may be of the electronic, magnetic, optical, electromagnetic, infrared, or semiconductor type.

In any case, the solution according to the present disclosure lends itself to be carried out with a hardware structure (for example, integrated in a chip of semiconductor material), or with a combination of software and hardware. The system of the invention is particularly suitable for the prevention and/or treatment of the respiratory distress syndrome (RDS) of the neonate (nRDS) However, it could be advantageously utilised for the prevention and/or treatment of the adult/acute RDS (ARDS) related to a surfactant-deficiency or dysfunction as well as of conditions in which respiratory distress may be present as a consequence of, for instance, meconium aspiration syndrome, pulmonary infection (e.g. pneumonia), direct lung injury and bronchopulmonary dysplasia.

Advantageously, the system of the invention is applied to pre-term neonates who are spontaneously breathing, and preferably to extremely low birth weight (ELBW), very-low-birth-weight (VLBW), and low-birth weight (LBW) neonates of 24-35 weeks gestational age, showing early signs of respiratory distress syndrome as indicated either by clinical signs and/or supplemental oxygen demand (fraction of inspired oxygen ($FiO_2$)>30%).

More advantageously, nasal Continuous Positive Airway Pressure (nCPAP) is applied to said neonates, according to procedures known to the person skilled in the art.

Preferably a nasal mask or nasal prongs are utilised. Any nasal mask commercially available may be used, for example those provided by The CPAP Store LLC, and the CPAP Company.

Nasal CPAP is typically applied at a pressure comprised between 1 and 12 cm water, preferably 2 and 8 cm water, although the pressure can vary depending on the neonate age and the pulmonary condition.

Other non-invasive ventilation procedures such as nasal intermittent positive-pressure ventilation (NIPPV), High Flow Nasal Cannula (HFNC), and bi-level positive airway pressure (BiPAP) can alternatively be applied to the neonates.

Possible alternative embodiments include the following:

A computer implemented method for delivering an atomized medicament to a spontaneously breathing patient including:

selectively activating first pump means for providing in the retropharyngeal cavity by means of a multi-channel flexible catheter a low pressure column of liquid medicament through at least a first channel of the multi-channel catheter;

selectively activating second pump means for providing a pressurized flow of gas through at least a second channel of the multi-channel catheter;

providing a continuous flow of pressurized water solution through at least a third channel;

detecting, by means of a pressure sensor being connected to the at least third channel, the inspiration activity of the patient;

wherein the liquid column of medicament is broken into a plurality of particles when the liquid column and the pressurized flow of gas meet in the retropharyngeal cavity, so that the atomized medicament is delivered into the patient's lungs; and wherein the step of providing liquid medicament through at least a first channel of the multi-channel catheter is performed only during the inspiration activity.

A computer program for implementing the steps of the above computer implemented method, when the program is executed on a computer.

A method for preventing and/or treating a respiratory distress syndrome in spontaneously breathing patient, said method comprising the step of delivering an atomized pulmonary surfactant medicament to the retro-pharyngeal region of the patient by means of a multi-channel flexible catheter a low pressure column of liquid medicament through at least a first channel of the multi-channel catheter and a pressurized flow of gas through at least a second channel of the multi-channel catheter; wherein the liquid column of medicament is broken into a plurality of particles when the liquid column and the pressurized flow of gas meet in the pharyngeal cavity further comprising the step of detecting by means of a pressure sensor, being connected to at least a third channel adapted to convey a flow of water solution in the retro-pharyngeal region, the inspiration activity of the patient; wherein said step of providing is performed only during the inspiration activity.

The method of preventing described above wherein nasal Continuous Positive Airway Pressure (nCPAP) with a nasal device such as a mask or prongs is applied to the patient.

The invention is now illustrated by means of the following non/limiting examples:

EXAMPLES

Example 1

In Vivo Efficacy

In vivo efficacy of atomized surfactant (in this example poractant alfa, as defined above) was evaluated in preterm newborn rabbits at the 27th day of gestation (term=31±1 days). The model chosen closely resembles the conditions of premature babies affected by RDS in that the lungs of these animals are not yet able to produce their own surfactant, but can warrant gas exchange so that they can expand in response to exogenous surfactant administration.

Treatments were intratracheally given at 2 ml/kg volume, corresponding to 160 mg/kg dose. Foetuses, paralyzed with pancuronium bromide (0.02 mg i.p.), were then placed in the plethysmograph system at 37° C. and ventilated with pure oxygen at constant pressure (frequency 40/min, inspiration/expiration ratio 60/40). No positive end-expiratory pressure (PEEP) was applied. An "opening" pressure of 35 cmH$_2$O was first applied for 1 min to overcome initial resistance due to capillarity in finer conducting airways. It was then followed by 15 min at 25 cmH$_2$O, 5 min at 20 cmH$_2$O, 5 min at 15 cmH$_2$O and again at 25 cmH$_2$O for the final 5 min. Respiratory flow was measured every 5 min by a Fleish tube connected to each chamber of the plethysmograph system. Tidal volume (Vt) was automatically obtained by integration of the flow curve.

Two sets of experiments were performed.

In the first set, five samples (1 ml each) have been received. The pulmonary surfactant administered at each samples is respectively: not atomized poractant alfa, poractant alfa atomized at an air pressure of 0.0, 0.2, 0.5 and 0.8 bar. The pulmonary surfactant has been atomized using the preferred embodiment of the present invention.

In this set of experiments a control group without any treatment was included.

All the atomized samples, including that passed through without any pressure applied, resulted as effective as not atomized poractant alfa ($P<0.05$, one-way ANOVA followed by Tukey's test; Graphpad Prism). No statistically significant difference was found between the different conditions of atomization.

In the second set, three samples (1 ml each) have been received. The pulmonary surfactant administered at each samples is respectively: non-atomized poractant alfa, poractant alfa atomized at an air pressure of 0.2, 0.5 and 0.8 bar.

In this set of experiments two further groups were included, a control group without any treatment and a group treated with a batch of poractant alfa already released to the market.

The same results were observed in the second set of experiments.

Figure 7:
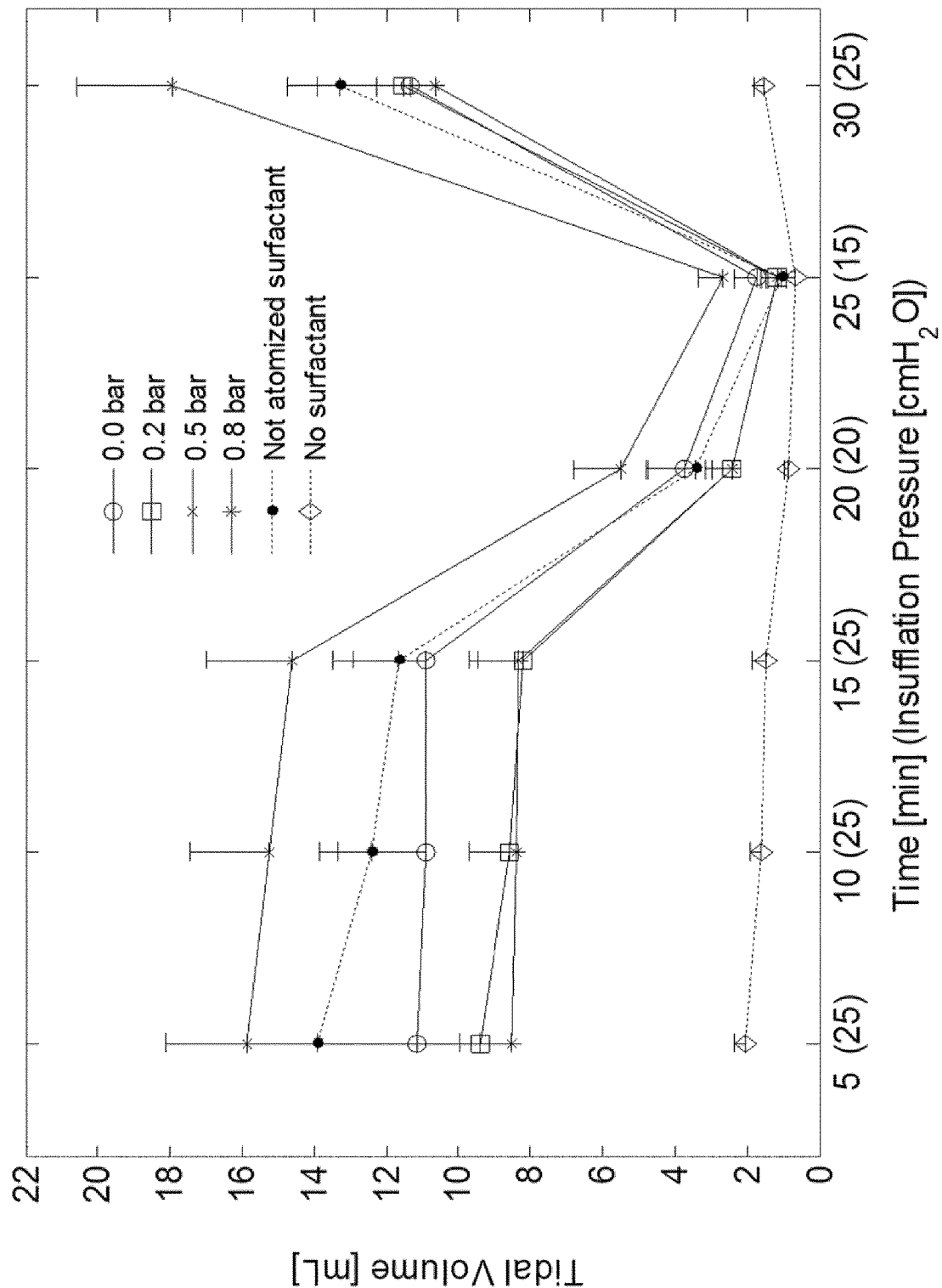

As the results were consistent in the two sets, the data have been pooled (FIG. 7). Statistical analysis of these data confirmed the previous results.

In conclusion the passage through the atomizer, using the preferred embodiment of this invention, does not affect poractant alfa efficacy in premature rabbit foetuses.

In particular atomization at pressures between 0.2 and 0.8 bar does not significantly affect poractant alfa efficacy and the application of 0.5 bar seems the most suitable although no statistically significant difference has been observed between different atomization conditions.

Example 2

Deposition Study

1. Groups

Old piglets, weighing between 0.8-2.0 kg, were used.

1.1 Insure Group (Control)

Under sedation with dexmedetomidine and ketamine and after topical anaesthesia of the larynx with lidocaine spray, the piglets were orally intubated Anaesthesia was supplemented by small doses of iv. propofol, as needed. Tube position was confirmed by bilateral auscultation of the lungs and careful assessment of the endotracheal tube depth. The piglets were laid on the side determined by the randomization protocol. Curosurf® was thoroughly mixed with 300 MBq of Tc-labelled nanocolloid and the animals received 200 mg/kg Curosurf® (80 mg/mL) instilled through a catheter advanced through the tube, ending exactly 5 mm beyond its tip. After Curosurf® instillation, the lungs were recruited with PS-ventilation (pressure-support, 4-8 $cmH_2O$ over PEEP) and PEEP 10 $cmH_2O$ for 1 min followed by PS med 4 $cmH_2O$ PEEP via the endotracheal tube for at least 30 min, at the end of which the animals were moved to the gamma camera for assessment of lung deposition of the Tc-labeled surfactant.

1.2 Nasal-CPAP, Group with the Catheter According to the Invention

The procedure was carried out as follows: piglets inhaled 10 mg of lidocaine and lidocaine gel was applied in the oropharynx just before the insertion of a Mayo oropharyngeal atomization cannula. The piglets were then laid on one side according to the randomization protocol, and correct positioning of the oropharyngeal cannula just above the larynx entrance was assessed by fiberbronchoscopy. Curosurf® was thoroughly mixed with 300 MBq of Tc-labeled nanocolloid and the animals received a total of 200 mg/kg Curosurf® (80 mg/mL) through an atomization catheter placed inside the oropharyngeal airway. The surfactant atomization procedure was divided in 4 stages (doses): each stage consisted in the delivery of one fourth of the total surfactant dose with the piglet breathing spontaneously on nasal-CPAP (via special "snout-mask", see details in methods), followed by 5 minutes of PS-ventilation with PEEP (via snout-mask) to avoid atelectasis and promote delivery of the surfactant to the lower airways. When all the surfactant had been delivered, the oropharyngeal cannula was removed and the piglet received PS-ventilation for 15 min. $FiO_2$ was adjusted to maintain saturation above 85%. To secure the airway under transportation to the gamma camera and scintigraphy, the animals were endotracheally intubated and manually ventilated with a Laerdal Silicone Resuscitator.

2. Methods

The piglets were premedicated with i.m. ketamine, midazolam, and atropine, an ear vein was cannulated, and the animals were sedated with a continuous iv. infusion of dexmedetomedine and ketamine. Sedation was supplemented with small intermittent boluses of iv. propofol when needed. An arterial catheter was placed in the femoral artery under local anaesthesia. Invasive blood pressure, pulse oximetry, cerebral oximetry (INVOS), and the diaphragmatic electrical activity (NAVA catheter) were monitored in all animals.

Blood gases were taken after preparation, before the start of surfactant administration, 15 min after the start of surfactant administration, and 2 min after the end of surfactant administration.

Group-assignment was random, and arranged so that pigs from the same litter were distributed evenly among the groups, when possible. The piglets were placed on the right or left side during surfactant administration according to randomization.

The following groups of piglets receiving Curosurf® 2.5 mL/kg (80 mg/mL) were investigated:

1—Nasal-CPAP, atomization with the catheter according to the invention: nasal-CPAP+Curosurf® delivery via a custom-made placed in the oropharynx, just above the laryngeal entrance and epiglottis.

2—"Insure protocol": Curosurf® instilled through an endotracheal tube, PS-ventilation via the endotracheal tube in a spontaneously breathing animal for at least 30 min.

2.1 Ventilation

In the nasal-CPAP groups, a special "snout-mask" enclosing the nostrils of the piglet was created in the laboratory with a "glove finger" and an endotracheal tube connector. This "snout-mask" helped to reduce leaks from the CPAP-system and seemed to offer more comfort to the animals which, in that way, required less anaesthesia. This mask was connected to the Y-piece of the ventilator tubing, and CPAP was generated by a SERVO-i ventilator (Maquet, Sweden). Depending on the piglets breathing pattern and degree of airway obstruction, the ventilator was adjusted to maintain a continuous positive airway pressure (CPAP) of 4-8 cm $H_2O$, with an inspired oxygen fraction ($FiO_2$) of 40% adjusted during treatment to keep oxygen saturation above 85%. As far as possible, the mouth was kept closed. At the end of the procedure, the piglets received PS-ventilation for 15 min before intubation and transportation to the gamma camera.

In the Insure group, a SERVO-i ventilator was used for PS-ventilation with PEEP of 10 $cmH_2O$ for 1 min after instillation followed by PS with PEEP 4 $cmH_2O$. The $FiO_2$ was 40%.

2.2 Measurement of Surfactant Distribution

The volume of Curosurf® to be delivered by atomization to each piglet was 2.5 mL/kg (80 mg/mL), but the priming of the delivery catheter and syringe required an average of 2.5 mL extra surfactant/pig; therefore, the Tc-labelled nanocolloid dose was increased to 300 MBq in this study (as compared to 200 MBq in our previous studies with Chiesi). The activity of the Tc-labelled nanocolloid was measured in a radiation counter. For each piglet, 300 MBq of Technetium-labelled nanocolloid particles were thoroughly mixed with Curosurf® immediately prior to "catheter priming".

The distribution of the atomized or instilled surfactant was studied with gamma scintigraphy. Images were taken before and after i.v. injection of Tc-labelled macro-aggregated human serum albumin (MAA), a substance that is trapped in the lung capillaries, allowing delineation of the lung fields. In addition, the MAA injection was used for calibrating the images. That way, the amount of Tc-labelled nanocolloid, deposited in the lungs, could be determined and, by inference, also the amount of deposited surfactant.

Before transportation to the gamma camera the animals were intubated to secure the airways, and to prevent the development of atelectasis and hypoventilation.

3. Results

The main outcome of the trial is the percentage of Curosurf® deposited into the lung, which can be inferred by the radioactivity stated by scintigraphy according to methods known to those skilled in the art.

3.1 Deposition Results

Results in this section are presented as median (range), if not otherwise stated. By manual segmentation of the images it has been possible to separate the regions in which the surfactant had deposited into four compartments: retropharynx, trachea, lungs, and stomach. In table 1 are reported the mean values for each compartment and the relative standard deviation (std).

TABLE 1

|  | percentage | |
|---|---|---|
|  | mean | Std |
| lungs | 48.5 | 13.5 |
| trachea | 13.5 | 1.7 |

TABLE 1-continued

|  | percentage | |
|---|---|---|
|  | mean | Std |
| pharynx | 11.1 | 4.3 |
| stomach | 9.1 | 8.4 |

By looking at this table it is possible to appreciate that more than 48% of surfactant is deposited into the lungs, otherwise less than 10% reaches the stomach.

Further analysis may be performed introducing a second compartmentalization as explained in more details here. The surfactant into trachea will flow into the lungs, while the surfactant deposited into the retropharynx is expected to be swollen and deposited into the stomach; therefore it is possible to define: 1) respiratory compartment that is given by the sum of the trachea and of the lungs and 2) the remaining compartment that is given by the sum of the surfactant into the stomach and the one found into the pharynx.

By this approach is possible to calculate the percentage of surfactant that reaches the respiratory compartment on the total that enters the body of the piglet. Table 2 reports the results

TABLE 2

| piglet | respiratory compartment/total [%] |
|---|---|
| #1 | 62.6 |
| #2 | 66.9 |
| #3 | 67.8 |
| #4 | 72.4 |
| #5 | 62.4 |
| #6 | 84.4 |

The total amount of surfactant that reaches the respiratory compartment has a mean value of 69.4% with a standard deviation of 8.2%, the individual values range from 62.4% to 84.4%, which means that about the 70% of the surfactant is deposited into the respiratory compartment.

In conclusion the results of the trial states that a significant amount of surfactant is deposited into the lung compartment, more than 61%. This result can be addressed both to the delivery approach, that is to atomized surfactant into the pharynx and to the high performances of the device that allows the administration of surfactant just during inspiration (95%).

Example 3

In Vivo Study in Pre-Term Lambs

The aim of this study was to compare the effect of atomisation of exogenous surfactant during spontaneous breathing whilst on CPAP with CPAP alone in a pre-term lamb model of neonatal respiratory disease.

1. Animals

Date-mated Border-Leicester ewes were studied at 130-134 d gestation. Ewes were pre-medicated with ketamine (250 mg) and xylazine (3 mg), anaesthetized with nitrous oxide, isoflurane and propofol, intubated and catheterized with arterial and venous catheters. Light anesthesia was maintained with nitrous oxide, a propofol infusion and the lowest possible isoflurane concentration (<2%), and the animal ventilated on SIMV+pressure support, set rate 12-15 bpm, tidal volume 10 mL/kg, and initial $F_iO_2$ 0.4-0.5. An arterial blood gas sample was taken and ventilator rate, tidal volume and $F_iO_2$ adjusted accordingly. The animal placed supine and prepared for Caesarean delivery.

2. Pulmonary Surfactant Preparation

Surfactant was labeled with Samarium Oxide ($SmO_3$), using an ultrasonic mixer at a concentration of 0.33 mg $SmO_3$ per 3 mL (1×vial) Curosurf®.

3. Fetal Instrumentation

After delivery of the fetal head and neck via hysterotomy, 5 FG catheters were placed in the neck vessels using a cut-down technique. The neck wound is sutured and infiltrated with bupivicaine. An arterial flow probe (Transonic) was implanted around a carotid artery for measurement of cerebral blood flow (CBF). Ewe anaesthesia from this point was maintained at the lowest possible propofol concentration, with the isoflurane reduced as close as possible to 0%. The fetal head was then dried, and 10% lignocaine spray (Xylocaine pump spray, Astra Zeneca, North Ryde, Australia) introduced into both nostrils, and applied to the vocal cords under direct laryngoscopic vision. Then the fetus was orally intubated with an Endotracheal tube size 4.0 cuffed, inserted 5 cm below vocal cords. An oesophageal balloon catheter, (size 10FG Foley catheter, Covidien, Mansfield, USA) was then inserted through the nares over 0.025 inch (0.64 mm) J-tipped guide wire and positioned in the esophagus. Position was checked to be mid-cervical and ~6 cm below cricoid cartilage when balloon inflated with 3 mL saline.

A 4.0 endotracheal tube (ETT) was then inserted into each other nares with a stylet/guide-wire to a depth of 7 cm and custom-built CPAP adaptor connected so the system could be connected to a standard T-piece F&P circuit.

With placental support maintained, the fetal chest was delivered, lung liquid drained with an intended recovery of at least 10 mL/kg. Then the ETT was removed and the snout wrapped snuggly with elastic bandage (Coban, 3M, St Paul, Minn.) to seal the mouth.

For lambs randomised to the Atomisation group (vide ultra) the atomisation delivery system was placed in the oro-pharynx such that the tip was 1.0 cm above the epiglottis and beyond the tongue. Through this device the atomisation catheter could later be advanced such that it was located free of oro-pharyngeal wall and upper airway structures (epiglottis) and oesophagus during atomisation delivery. Placement was performed under direct visual guidance using a fibre-optic scope and the insertion length marked on the device, which was then removed.

Finally, respiratory inductance plethysmography (RIP) bands were placed around the chest and abdomen. Prior to delivery the oropharynx was suctioned to remove any accumulated fetal fluid. EIT electrodes were also placed in some lambs using the methods we have published previously (Tingay et al Ped Res November 2013).

4. Groups 4.1 CPAP without surfactant: This included maintaining the lamb on a CPAP PEEP of 6-10 cm $H_2O$ (as required) for a minimum of 90-min after establishing CPAP and a maximum of 2.5-2.75 hr total study time.

4.2 Atomisation: Once established on CPAP the atomisation catheter according the invention was re-inserted into the oro-pharynx using the pre-determined measurements and secured with Coban after vigorous suction to clear secretions. The atomisation catheter was inserted and the system primed and checked. The $F_iO_2$ was increased by 0.1 de novo and the PEEP increased to 10 cm $H_2O$.

Atomisation of 200 mg/kg of Curosurf® was commenced if an arterial blood gas 15-min after inserting the system. After the atomisation period (45-75 min usually) the atomisation system was removed and the lamb managed on CPAP alone. The study continued until 2.5-2.75 hr of life and a minimum of 90 min of data after starting the atomisation.

4.3 Insure: A small group of lambs were allocated to receive the INSURE method (see Example 2). The three animals studied were transiently intubated after at least 15-min of stability on CPAP and 200 mg/kg Curosurf™ given via a closed delivery system during PPV with the Neopuff at a PIP 40 cm $H_2O$ and Rate 30-40 bpm. The animals were then extubated immediately to CPAP and managed as per the CPAP only group.

5. Post-Delivery Measurements

Peripheral oxygen saturation ($SpO_2$), heart rate, arterial blood pressure and rectal temperature were applied at birth and displayed continuously thereafter (HP48S, Hewlett Packard, Andover, Mass.). Tidal volume ($V_T$) and breathing pattern was measured with DC-coupled RIP (Respitrace 200™, NIMS Inc., North Bay Village, Fla.), sampling at 200 Hz using a method described in Tingay D G et at Crit Care Med. 2013; 41(1); 237-44.

Arterial blood gas analysis was performed periodically at 15-30 min intervals. CBF was measured from a flow probe (Transonic, AD Instruments, Sydney) placed around the carotid artery and signal quality maintained with ultrasonic gel as required.

6. Post-Mortem Analysis

The lung and trachea were removed intact from the thorax and inflated at 30 cm $H_2O$ for 15-s followed by 15 cm $H_2O$ for 15-30-s via an ETT (no leak) and Neopuff. Whilst inflated the lung was wrapped in alfoil and snap frozen inflated in liquid Nitrogen and stored at −20 C for analysis of $SmO_3$ concentration in the lung.

7. Data Acquisition and Analysis

Data were manually recorded with each arterial blood gas. $SpO_2$, heart rate, arterial blood pressure, delivered airway pressure, RIP sum, chest and abdominal waveforms, tidal volume and flow (intubated periods only), temperature and cerebral blood flow waveform were digitalised (PowerLab™ system) and recorded at 1000 Hz in LabChart™ V7 (AD Instruments, Sydney, Australia) for later analysis. EIT recordings of the pattern of tidal ventilation within the chest were made simultaneously. All data was stored in a Neonatal Research (MCRI) computer. Blood gas and manually recorded data were directly entered into an excel spreadsheet for integration with LabChart Data.

At each analysis point 30-s of stable respiratory data representative of the animals breathing pattern and condition at that time were extracted and the following parameters calculated:

1. Oxygenation: SpO2, $F_iO_2$, aA ratio (lower value representing worse lung disease) and $AaDO_2$.
2. $PaCO_2$
3. Applied PEEP (and PIP if applicable)
4. Heart rate, arterial blood pressure (mean, systolic and diastolic), cerebral blood flow waveforms. CBF pulsatile amplitude and minimum CBF was extracted using LabChart Peak Analysis software.
5. RIP (sum, chest and abdomen) waveform for the entire 30-s period. From this the respiratory rate was determined. The amplitude of the sum RIP data was used to determine the relative tidal volume ($V_T$) for each spontaneous breath, expressed in countless units (see Tingay D G et al Crit Care Med. 2013 January; 41(1), 237-44) and referenced to the RIP $V_T$ at t0 to determine change in relative $V_T$ over time.

6. Static lung mechanics using FOT and PV curves analysis.
7. The EIT data during the same 30-s period was reconstructed using a custom-built EIT analysis program that accounts for the unique shape of the lamb chest. The subsequent images were analysed in MatLab and AUSPEX to generate functional EIT scans of the distribution of tidal ventilation during the 30-s period in each of 32 gravity dependent (anterior to posterior) lung slices of the right and left hemithorax using the SD method reported in Frerichs I et al Am J Respir Crit Care Med. 2006; 174(7);772-9.

From these data, the pattern of fractional ventilation (compared to total $V_T$) was determined within the lung regions at t0, t60 (immediately after surfactant in Atomisation groups) and t90 (30-min after surfactant administration) and compared.

All statistical analysis was performed by MCRI was in PRISM (GraphPad Software, CA, USA).

Data was tested for normality and analysis performed with parametric or non-parametric tests as appropriate. Longitudinal comparisons between groups were analysed with 2-way ANOVA with Sidak post tests using time and surfactant strategy as variables.

Qualitative data was also reported, including lamb comfort score, interventions needed, patterns of breathing, complications and staff observations.

8. Results

Figure 8:
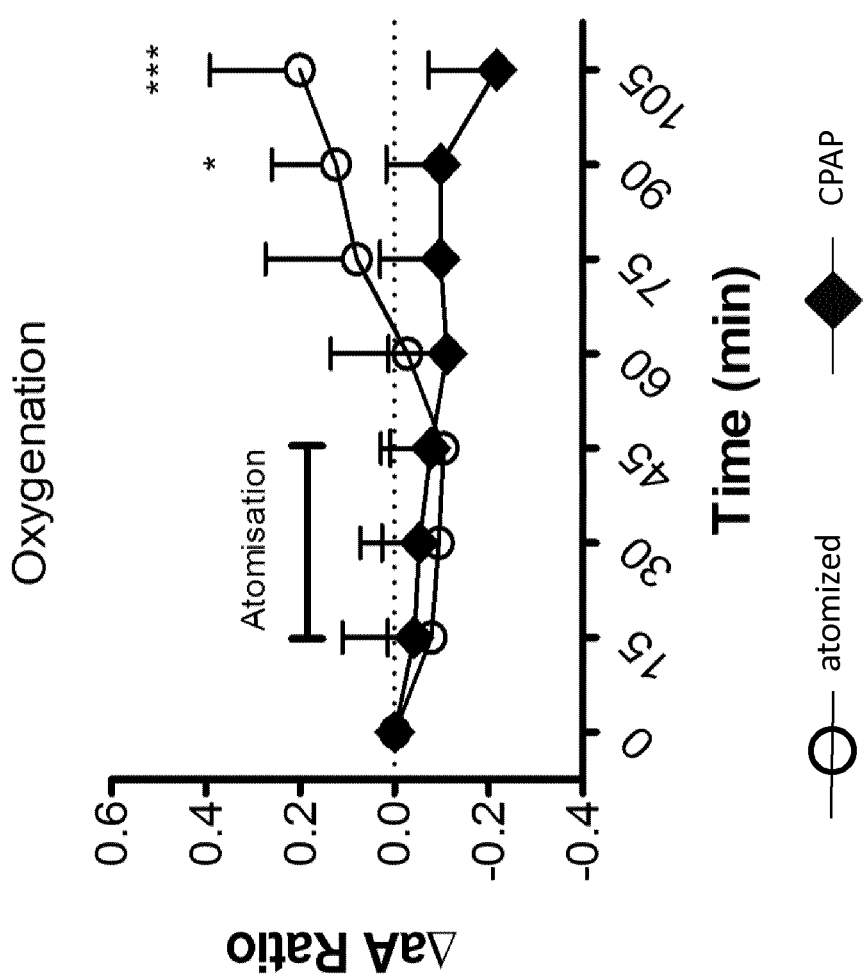

In most lambs the atomisation system of the invention was tolerated and showed a promising respiratory profile.in In particular, as it can be appreciated from FIG. 8, it appeared to improve the aA $O_2$ ratio compared to CPAP alone.

The invention claimed is:

1. A system specifically arranged to deliver a medicament comprising a pulmonary surfactant to spontaneously breathing pre-term neonate patients, comprising:
    a catheter specifically adapted to have a distal end thereof provided in the retro-pharyngeal region of the spontaneously breathing pre-term neonate patient without the presence of an intubation tube and a ventilator, the catheter including at least a first channel adapted to convey in the spontaneously breathing pre-term neonate patient's pharyngeal region a flow of liquid medicament including the pulmonary surfactant in the form of a column, and at least a second channel adapted to convey in the spontaneously breathing pre-term neonate patient's pharyngeal region a pressurized flow of gas,
    a first pump connected to a first end of the at least first channel, that creates a pressure which pushes the column of liquid medicament towards the second end of the at least first channel;
    a second pump connected to a first end of the at least second channel, that creates the flow of pressurized gas, wherein the catheter outputs the column of liquid medicament and the pressurized flow of gas according to an air blasting approach such that when the column of liquid medicament and the pressurized flow of gas meet in the pharyngeal cavity, the column of liquid medicament is broken into a plurality of particles to cause an atomized medicament to be delivered into the spontaneously breathing pre-term neonate patient's lungs; and
    a pressure detecting system, separate from the at least first channel and the at least second channel, adapted to sense pressure swings in the spontaneously breathing pre-term neonate patient's pharyngeal cavity, such sensing being used to determine whether the spontaneously breathing pre-term neonate patient is in an inspiration or in an expiration phase, wherein
    the first pump is selectively activated only during inspiration phase,
    the pressure detecting system includes:
        a third channel adapted to convey a flow of an aqueous solution in the retro-pharyngeal region of the throat of the spontaneously breathing pre-term neonate patient,
        a third pump connected to a first end of the third channel that creates the flow of the aqueous solution, and
        a pressure sensor connected to the third channel that measures a value indicative of pressure on the flow of the aqueous solution,
    the pulmonary surfactant is poractant alfa,
    the at least second channel includes a plurality of channels arranged around the at least first channel,
    the at least first channel enlarges towards an end of the at least first channel, and
    respective cross sections of the plurality of channels decrease towards ends of the channels, the decrease corresponding to the enlargement of the at least first channel.

2. The system according to claim 1, wherein the third channel is outside of the catheter, axially offset and spaced apart from the at least first channel and the at least second channel.

3. The system according to claim 1, wherein the catheter is made of flexible plastic material.

4. The system according claim 1,
    wherein the at least second channel includes a plurality of channels arranged around the at least first channel, and
    wherein the third channel is one of the channels arranged around the at least first channel.

5. The system of claim 1, wherein an external cross section of the third channel is equal to or lower than 2.5 mm.

6. The system according to claim 1, wherein the pressurized flow of gas includes air.

7. The system according to claim 1, wherein the aqueous solution includes a physiological saline (0.9% w/v sodium chloride) aqueous solution, buffered at a physiological pH.

8. The system according to claim 1, wherein the catheter is adapted to provide the plurality of particles for the atomized medicament having droplet median diameter of between 20-100 micron.

9. The system according to claim 1, wherein
    an output flow for the first pump is 9-18 ml/hr, and
    an output flow for the second pump is less than 1 L/min.

* * * * *